(12) United States Patent
Kawagishi

(10) Patent No.: US 9,715,657 B2
(45) Date of Patent: Jul. 25, 2017

(54) INFORMATION PROCESSING APPARATUS, GENERATING METHOD, MEDICAL DIAGNOSIS SUPPORT APPARATUS, AND MEDICAL DIAGNOSIS SUPPORT METHOD

(71) Applicant: CANON KABUSHIKI KAISHA, Tokyo (JP)

(72) Inventor: Masami Kawagishi, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 221 days.

(21) Appl. No.: 14/147,898

(22) Filed: Jan. 6, 2014

(65) Prior Publication Data

US 2014/0195472 A1    Jul. 10, 2014

(30) Foreign Application Priority Data

Jan. 9, 2013  (JP) ................................ 2013-002094
Mar. 19, 2013  (JP) ................................ 2013-057306

(51) Int. Cl.
*G06F 19/00* (2011.01)
*G06N 5/04* (2006.01)

(52) U.S. Cl.
CPC ............. *G06N 5/04* (2013.01); *G06F 19/345* (2013.01)

(58) Field of Classification Search
None
See application file for complete search history.

(56) References Cited

U.S. PATENT DOCUMENTS

| 7,095,979 B2 * | 8/2006 | Stout ..................... G09B 23/02 434/353 |
| 8,433,661 B2 | 4/2013 | Eggert et al. ................... 706/12 |
| 2004/0193036 A1 | 9/2004 | Zhou et al. ................... 600/407 |
| 2005/0010445 A1 | 1/2005 | Krishnan et al. ................. 705/2 |

(Continued)

FOREIGN PATENT DOCUMENTS

| JP | A 2010-200840 | 9/2010 |
| JP | A 2010-262625 | 11/2010 |

(Continued)

OTHER PUBLICATIONS

EESR issued May 12, 2017 in counterpart European Patent Application 14150198.1 (Eng).

*Primary Examiner* — Alan Chen
*Assistant Examiner* — David H Kim
(74) *Attorney, Agent, or Firm* — Fitzpatrick, Cella, Harper & Scinto

(57) ABSTRACT

A medical diagnosis support apparatus includes a training data obtaining unit that obtains training data, an inference means candidate creating unit that creates a plurality of inference means candidates based on the training data, an inference performance evaluation unit that evaluates the performance of the plurality of inference means candidates based on the training data, an information validity evaluation unit that evaluates the validity of information presented by each of the plurality of inference means candidates based on the training data, and an inference means selection unit that selects an inference means from the plurality of inference means candidates based on the performance of the plurality of inference means candidates and the validity of the information presented by each of the plurality of inference means candidates.

23 Claims, 12 Drawing Sheets

(56) References Cited

U.S. PATENT DOCUMENTS

| | | | |
|---|---|---|---|
| 2010/0183217 A1* | 7/2010 | Seung | G06K 9/342 |
| | | | 382/156 |
| 2010/0332441 A1 | 12/2010 | Kawagishi et al. | 706/52 |
| 2011/0082712 A1 | 4/2011 | Eberhardt, III et al. | 705/4 |
| 2011/0199390 A1 | 8/2011 | Iizuka et al. | 345/629 |
| 2011/0213748 A1 | 9/2011 | Kawagishi | 706/52 |
| 2012/0041779 A1* | 2/2012 | Boroczky | G06Q 50/22 |
| | | | 705/2 |
| 2012/0136882 A1 | 5/2012 | Kawagishi et al. | 707/758 |
| 2012/0254101 A1 | 10/2012 | Kawagishi et al. | 706/52 |
| 2013/0158398 A1* | 6/2013 | Park | G06T 7/0014 |
| | | | 600/437 |
| 2013/0212056 A1 | 8/2013 | Kawagishi | 706/46 |
| 2013/0249903 A1* | 9/2013 | Isokawa | G06F 19/321 |
| | | | 345/419 |

FOREIGN PATENT DOCUMENTS

| | | |
|---|---|---|
| JP | A 2011-180845 | 9/2011 |
| WO | WO 2009/103156 | 8/2009 |
| WO | WO 2010/035161 | 4/2010 |

* cited by examiner

FIG. 4

| j | $I_j$ (FINDING NAME) | $j_k$ | $S_{jk}$ (STATE NAME) |
|---|---|---|---|
| 1 | SHAPE | 11 | ROUND |
| | | 12 | LOBULATE |
| | | 13 | IRREGULAR |
| 2 | LOBATION | 21 | STRONG |
| | | 22 | MEDIUM |
| | | 23 | WEAK |
| | | 24 | NONE |
| 3 | RADIAL SHAPE | 31 | STRONG |
| | | 32 | MEDIUM |
| | | 33 | WEAK |
| | | 34 | NONE |
| 4 | TRANSLUCENCY | 41 | YES |
| | | 42 | PSEUDO |
| | | 43 | NO |
| .... | | | |
| l | WRAP (RESPIRATORY SYSTEM) | l1 | YES |
| | | l2 | PSEUDO |
| | | l3 | NO |
| .... | | | |
| m | PAST ILLNESS | m1 | YES |
| | | m2 | NO |

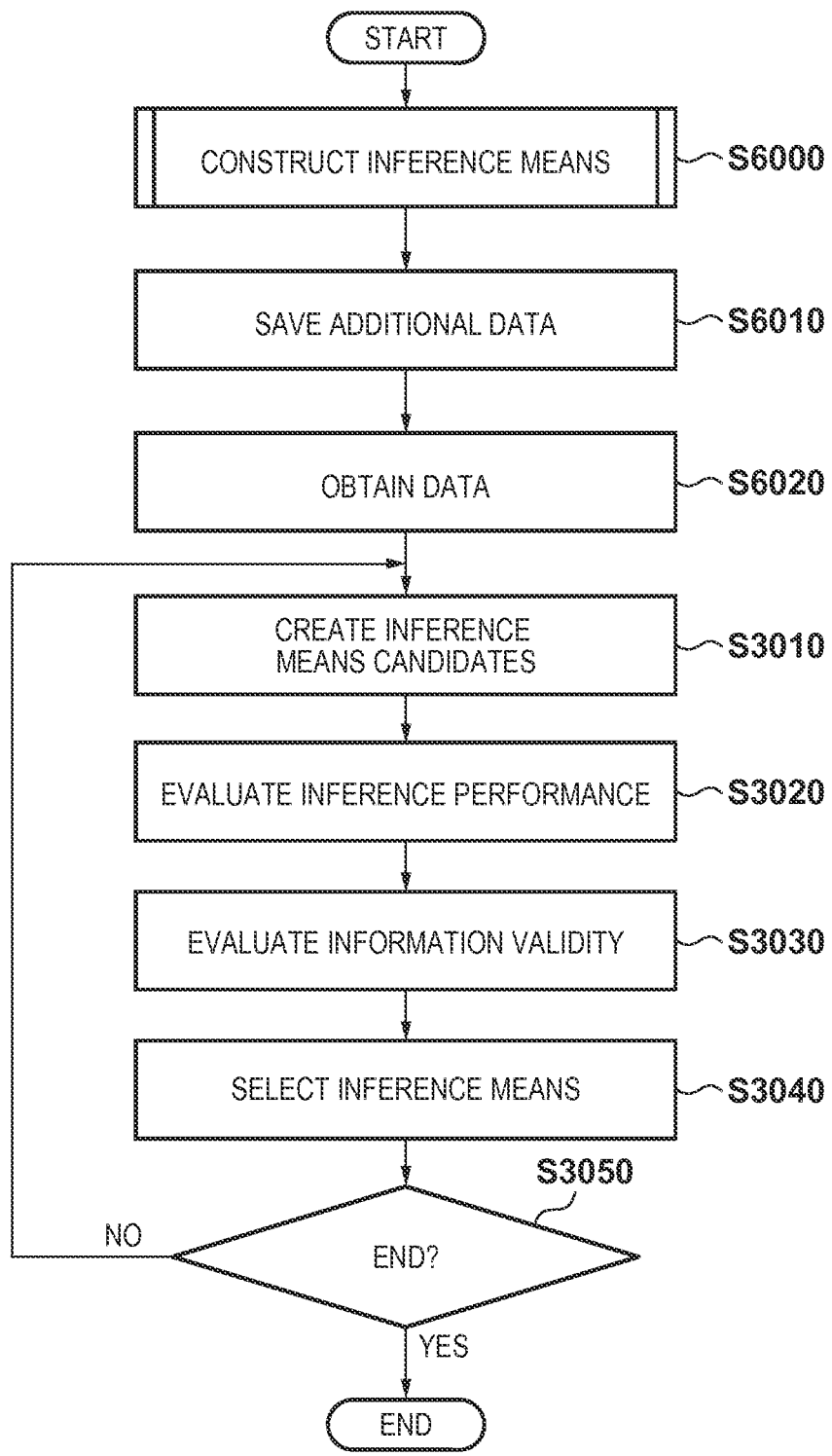

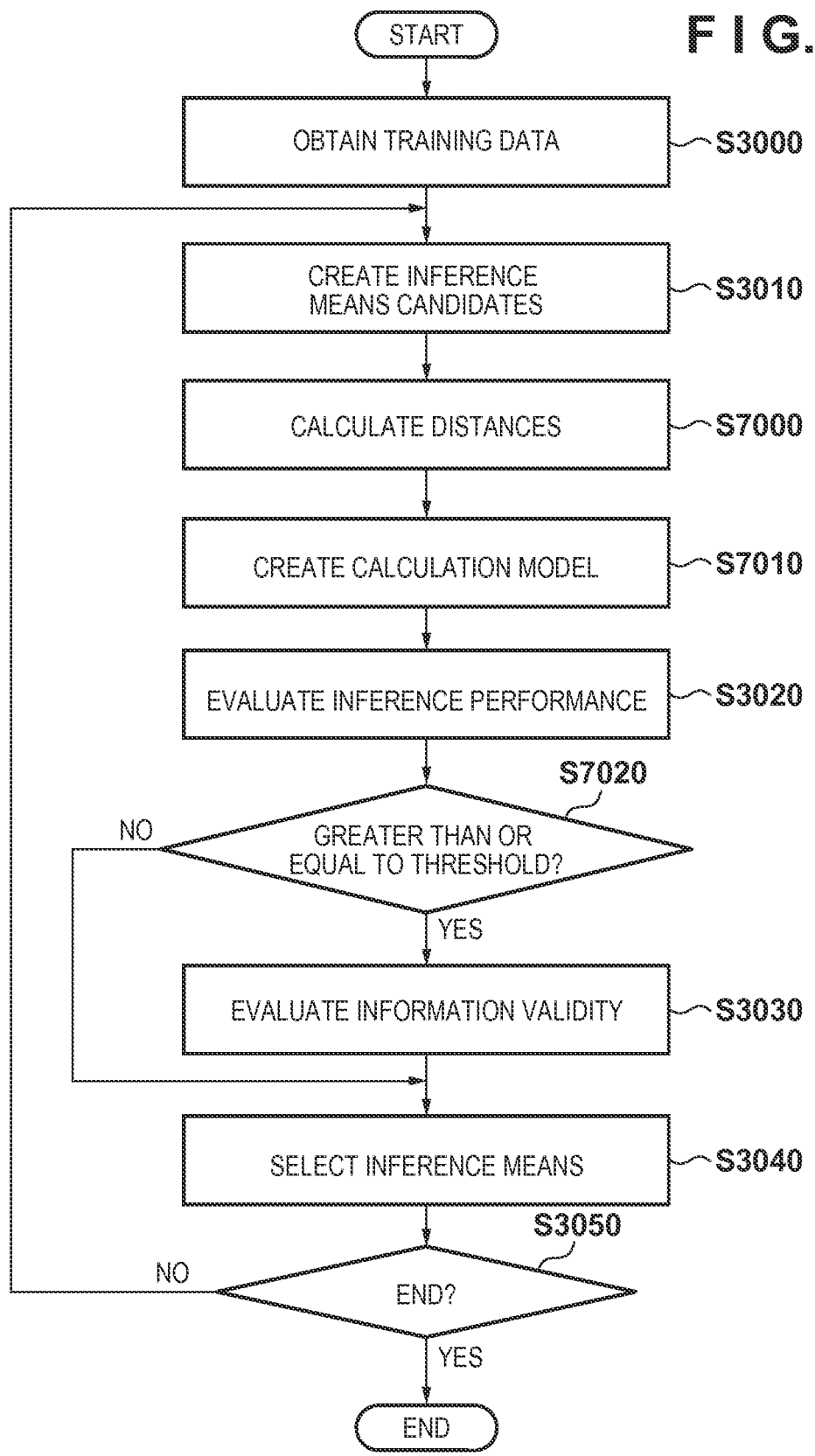

|   | D | $I_1$ | $I_2$ | $I_3$ | $I_4$ | $I_5$ | $I_6$ | $I_7$ | $I_i$ | $I_m$ |
|---|---|---|---|---|---|---|---|---|---|---|
| D | — | — | — | — | — | — | — | — | — | — |
| $I_1$ | 2 | — | — | — | — | — | — | — | — | — |
| $I_2$ | 1 | 1 | — | — | — | — | — | — | — | — |
| $I_3$ | 3 | 1 | 2 | — | — | — | — | — | — | — |
| $I_4$ | 4 | 2 | 3 | 1 | — | — | — | — | — | — |
| $I_5$ | 2 | 2 | 1 | 1 | 2 | — | — | — | — | — |
| $I_6$ | 1 | 3 | 2 | 3 | 4 | 2 | — | — | — | — |
| $I_7$ | 2 | 3 | 3 | 2 | 3 | 1 | 1 | — | — | — |
| $I_i$ | ∞ | ∞ | ∞ | ∞ | ∞ | ∞ | ∞ | — | — | — |
| $I_m$ | ∞ | ∞ | ∞ | ∞ | ∞ | ∞ | ∞ | ∞ | — | — |

F I G. 10
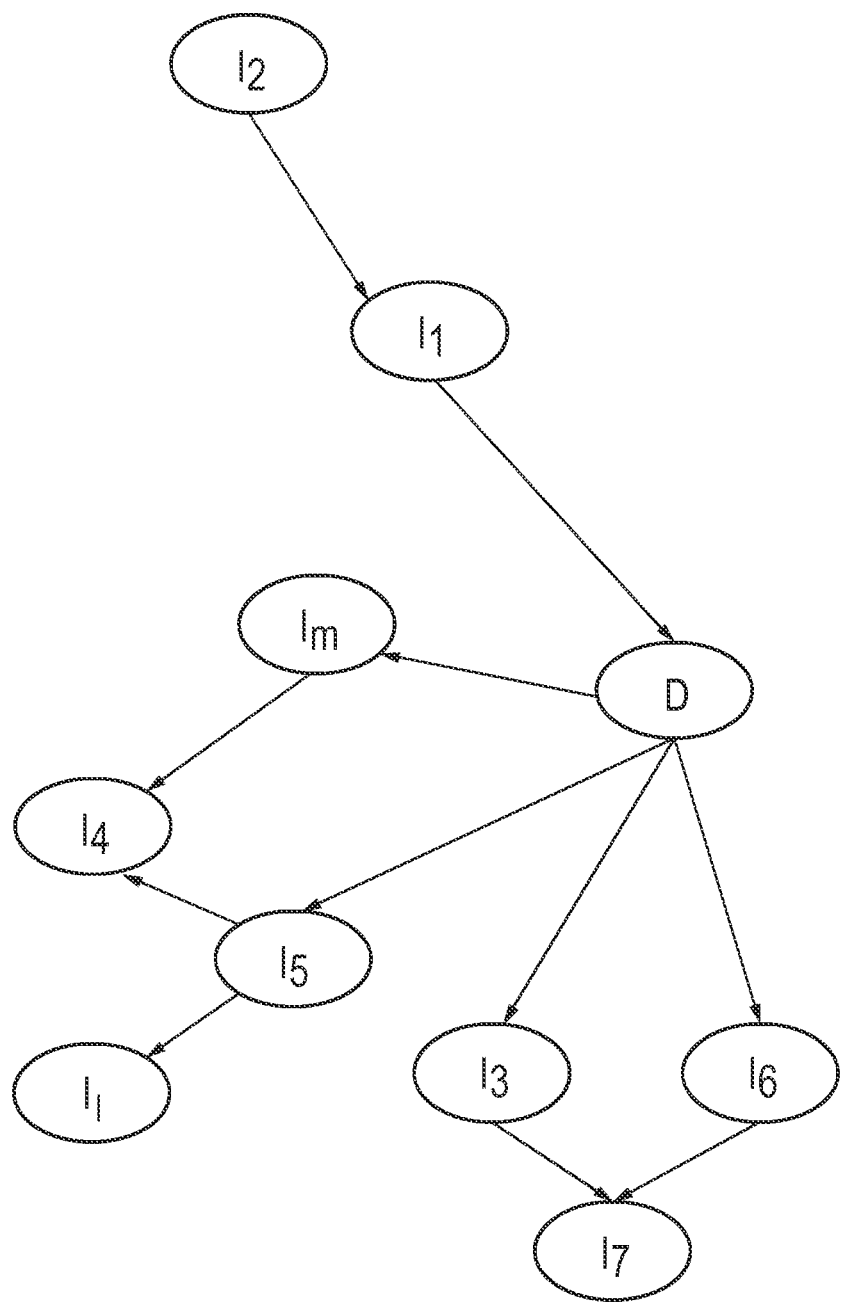

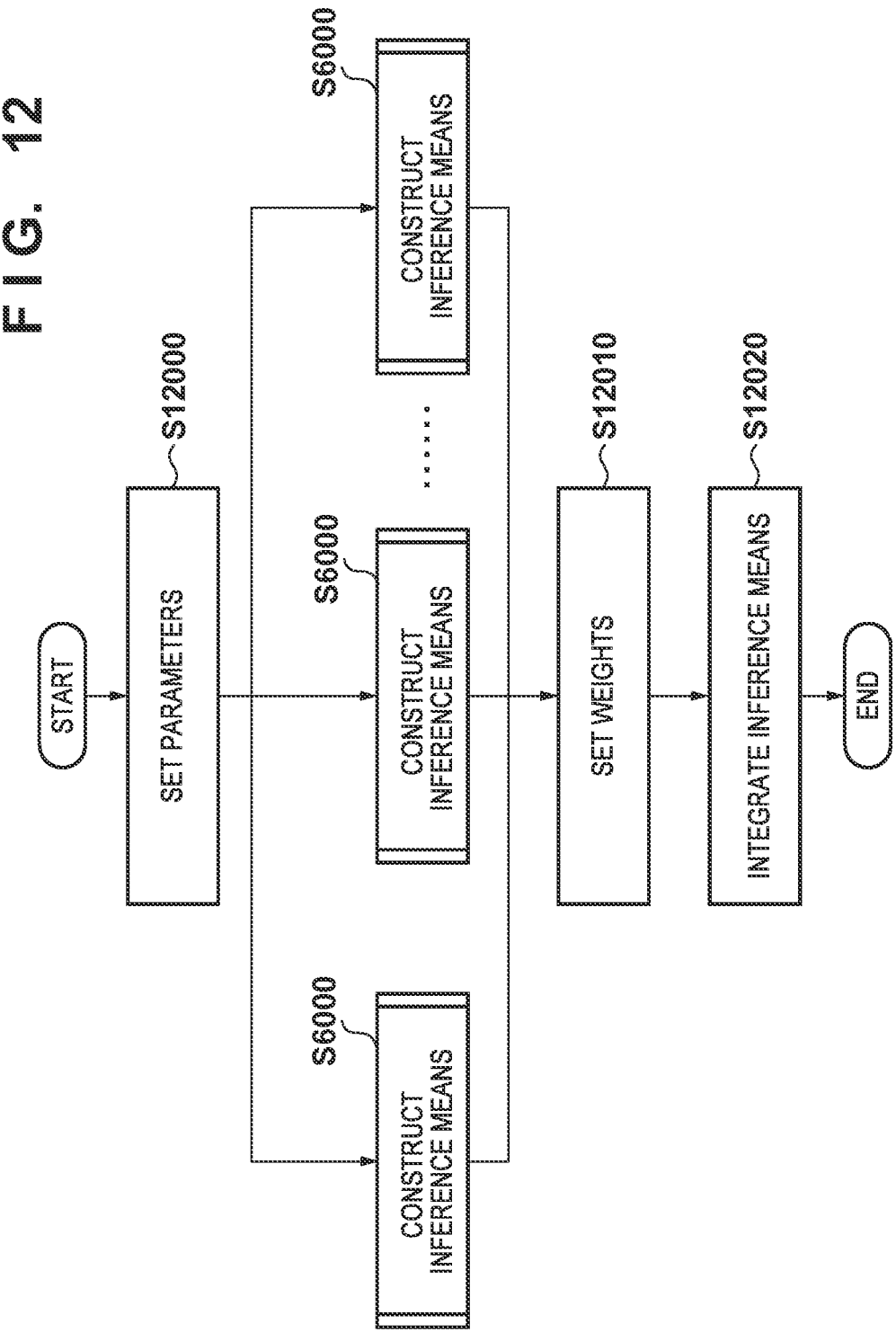

INFORMATION PROCESSING APPARATUS, GENERATING METHOD, MEDICAL DIAGNOSIS SUPPORT APPARATUS, AND MEDICAL DIAGNOSIS SUPPORT METHOD

BACKGROUND OF THE INVENTION

Field of the Invention

The present invention relates to information processing apparatuses, generating methods, medical diagnosis support apparatuses, and medical diagnosis support methods.

Description of the Related Art

In the field of medicine, an image-based diagnosis is performed by a doctor reading a medical image obtained using an imaging device such as an X-ray CT device, an MRI device, or the like and making a diagnosis of a condition based on the medical image. In an image-based diagnosis, an attending physician makes a request to interpret an image, and in response to the request, a doctor makes an overall judgment based on findings obtained from the image (called "image findings" hereinafter) and from various types of measured values and so on, and identifies symptoms of pathologic changes present in the image. Using the image findings, the measured values and so on, the doctor then consolidates the process leading to the diagnosis into an interpretation report for the attending physician who made the request.

Diagnosis support apparatuses for supporting such image-based diagnoses are being developed. For example, Japanese Patent Laid-Open No. 2010-200840 discloses a technique for obtaining an inference result using an inference means based on information that has been input (called "input information" hereinafter) and presenting negative information and positive information as support information in response to the obtained inference result. This makes it possible to present the inference result, as well as information that helped lead to the inference result based on the input information. Here, the inference means is also called as a inference model, which includes data structure for conducting inference, for example a mathematical expression implemented as a software data. An inference model is used to conduct inference to output an inference result based on the input data. For example a CPU (a central processing unit) conducts inference using the inference model to process the input data to output the inference result.

The inference means used in such an apparatus is often constructed using a machine-based learning technique. In this case, the inference means is constructed using training data (called "training data" hereinafter). A general method for constructing the inference means comprises constructing a plurality of inference means and selecting the optimal inference means using an index, such as an information amount reference, for evaluating the performance of the inference means. Meanwhile, although the training data is used under the assumption that the training data is the same as data used during operation (the latter being called "additional data"), there are cases where the training data increasingly diverges from the additional data as operations progress. Accordingly, attempts are being made to reconstruct and update the inference means using the additional data in order to suppress such divergence from the additional data. For example, Japanese Patent Laid-Open No. 2010-262625 discloses a technique that uses estimated values obtained from the additional data and applies the inference means in a progressive manner.

Japanese Patent Laid-Open No. 2010-200840 discloses a technique that uses an already-constructed inference means, and does not disclose how the inference means has been constructed. In light of the purpose of the inference means, it is desirable to present information of validity as the information that helped lead to the inference result. Furthermore, it is desirable to periodically update the inference means in order to prevent divergence from the additional data during operation.

However, typical methods for constructing the inference means focus only on the performance of the inference means, and have not considered how the most valid information can be presented. In addition, there is generally thought to be a tradeoff between the performance of the inference means and the capability to display the most valid information, and so it has been difficult to construct an inference means that meets both needs when focusing only on the performance of the inference means.

Although an inference means that periodically restores the performance of the inference means can be constructed in the case where the technique of Japanese Patent Laid-Open No. 2010-262625 is integrated as well, it is difficult to periodically construct an inference means that also takes the validity of the information presented into consideration.

In light of the aforementioned problems, it is an object of the present invention to provide a medical diagnosis support technique capable of constructing an inference means that takes into consideration both the performance of the inference means and the validity of presented information.

SUMMARY OF THE INVENTION

According to one aspect of the present invention, there is provided an information processing apparatus providing an inference means for outputting a diagnosis inferred for a medical case and reason information used to infer the diagnosis, the apparatus comprising: a first obtainment unit configured to obtain values indicating an inference performance for each of a plurality of inference means based on a group of first correct data including a correct diagnosis for the medical case; a second obtainment unit configured to obtain values indicating a validity of the reason information used in the inference output by each of the plurality of inference means, based on a group of second correct data that includes information to be identified in a case for which the correct diagnosis has been provided; and a third obtainment unit configured to obtain at least one inference means from the plurality of inference means based on the values indicating the inference performance and the values indicating the validity.

According to another aspect of the present invention, there is provided a generating method for generating an inference means that outputs a diagnosis inferred for a medical case and reason information used to infer the diagnosis, the method comprising: a first obtainment step of obtaining values indicating an inference performance for each of a plurality of inference means based on a group of first correct data including a correct diagnosis for the medical case; a second obtainment step of obtaining values indicating a validity of the reason information used in the inference output by each of the plurality of inference means, based on a group of second correct data that includes information to be identified in a case for which the correct diagnosis has been provided; and a generating step of generating at least one inference means from the plurality of inference means based on the values indicating the inference performance and the values indicating the validity.

According to still another aspect of the present invention, there is provided a medical diagnosis support apparatus comprising: a training data obtainment unit configured to obtain training data; a candidate creating unit configured to create a plurality of inference means candidates based on the training data; an inference performance evaluation unit configured to evaluate the performance of the plurality of inference means candidates based on the training data; an information validity evaluation unit configured to evaluate the validity of information presented by each of the plurality of inference means candidates based on the training data; and a selection unit configured to select an inference means from the plurality of inference means candidates based on the performance of the plurality of inference means candidates and the validity of the information presented by each of the plurality of inference means candidates.

According to another aspect of the present invention, there is provided a medical diagnosis support method for a medical diagnosis support apparatus, the method comprising: an obtainment step of obtaining training data; a creating step of creating a plurality of inference means candidates based on the training data; an inference performance evaluation step of evaluating the performance of the plurality of inference means candidates based on the training data; an information validity evaluation step of evaluating the validity of information presented by each of the plurality of inference means candidates based on the training data; and a selection step of selecting an inference means from the plurality of inference means candidates based on the performance of the plurality of inference means candidates and the validity of the information presented by each of the plurality of inference means candidates.

According to the present invention, an inference means that takes into consideration both the performance of the inference means and the validity of presented information can be constructed. In addition, information that continues to be appropriate even after operations have started can be presented by updating the inference means after the start of operations.

Further features of the present invention will become apparent from the following description of exemplary embodiments (with reference to the attached drawings).

BRIEF DESCRIPTION OF THE DRAWINGS

FIG. 4 is a diagram illustrating an example of image findings and clinical information.

FIG. 6 is a diagram illustrating a processing sequence performed by a medical diagnosis support apparatus according to a second embodiment.

FIG. 7 is a diagram illustrating a processing sequence performed by a medical diagnosis support apparatus according to a third embodiment.

FIG. 10 is a diagram illustrating an example of a graph structure according to the third embodiment.

FIG. 12 is a diagram illustrating a processing sequence performed by a medical diagnosis support apparatus according to a fourth embodiment.

DESCRIPTION OF THE EMBODIMENTS

Hereinafter, a medical diagnosis support apparatus and a medical diagnosis support method according to embodiments of the invention will be described with reference to the drawings. However, it should be noted that the constituent elements denoted in the following embodiments are to be taken as examples only; the technical scope of the present invention is defined by the appended claims, and is not intended to be limited by the individual embodiments described hereinafter.

First Embodiment

A medical diagnosis support apparatus according to a first embodiment obtains medical information regarding a case to be diagnosed as input information and constructs an inference means that supports the diagnosis of the case.

Note that the following assumes that a plurality of image findings regarding an abnormal shadow in a lung and a past illness history, tumor marker values, and the like (called "clinical information" hereinafter) are obtained as training data and additional data using the medical diagnosis support apparatus. Based on the obtained information, an inference means suited to presenting (displaying) an inference result and information that influences the inference result is constructed, with the type of abnormality in the abnormal shadow (a diagnosis) serving as an inference target.

The inference target is of course not limited thereto, and the diagnosis, image findings, clinical information, and so on that can be input as described hereinafter are all no more than examples used to illustrate the processing steps performed by the medical diagnosis support apparatus.

Figure 1:
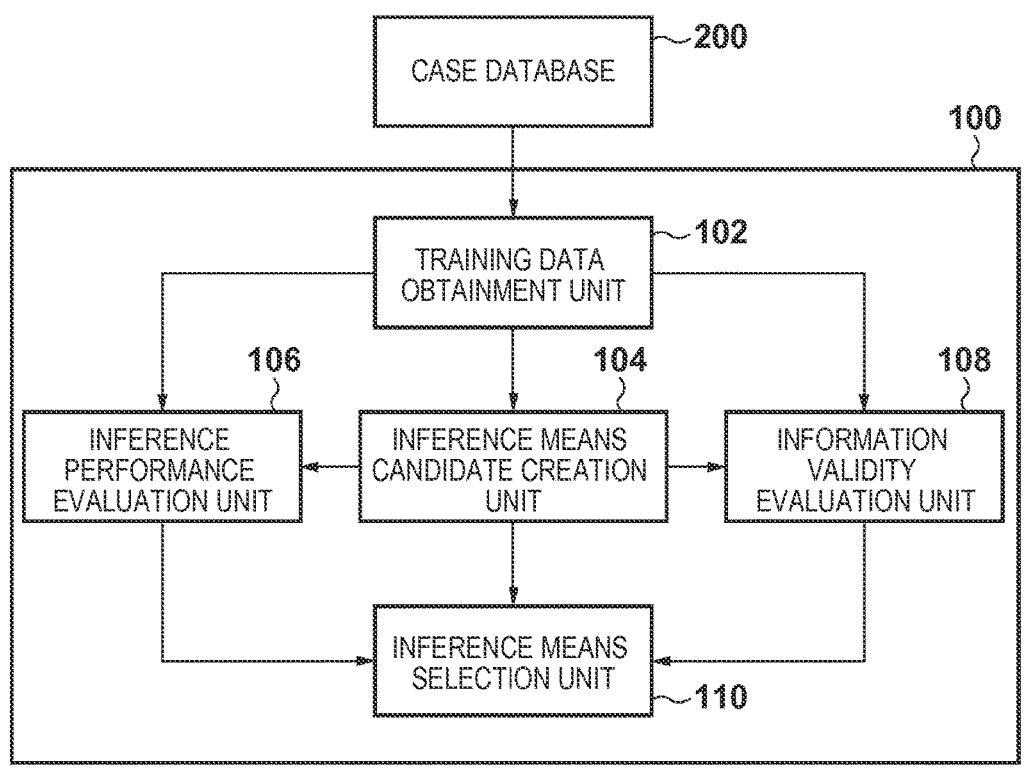
FIG. 1 is a diagram illustrating the functional configuration of a medical diagnosis support apparatus according to a first embodiment.

FIG. 1 is a diagram illustrating the functional configuration of the medical diagnosis support apparatus according to the first embodiment. A medical diagnosis support apparatus 100 according to the present embodiment is connected to a case database 200.

The case database 200 obtains, from a server (not shown), medical information (a medical image, electronic health record (EHR) information, and the like) of an abnormal shadow in a lung, for a case to be diagnosed. Alternatively, the apparatus may be connected to an external storage device, such as an FDD (flexible disk drive), an HDD (hard disk drive), a CD (compact disk) drive, a DVD (digital versatile disk) drive, an MO (magneto-optical) drive, a ZIP (compressed) drive, or the like, and the data may be obtained therefrom. The case database 200 stores information including a diagnosis and clues that led to the diagnosis for each case. This information may be automatically obtained from an electronic health record, an interpretation report, or the like, or may be obtained manually.

The medical diagnosis support apparatus 100 includes a training data obtainment unit 102, an inference means candidate creation unit 104, an inference performance evaluation unit 106, an information validity evaluation unit 108, and an inference means selection unit 110.

The training data obtainment unit 102 obtains medical information, a finalized diagnosis, and information of clues leading to the diagnosis for a plurality of cases regarding an abnormal shadow in a lung as training data from the case database 200 via a LAN (local area network) or the like. The training data obtainment unit 102 outputs the obtained information to the inference means candidate creation unit 104, the inference performance evaluation unit 106, and the information validity evaluation unit 108.

The inference means candidate creation unit 104 creates a plurality of inference means candidates based on the training data obtained from the training data obtainment unit 102. The inference means candidate creation unit 104 outputs the created inference means candidates to the inference performance evaluation unit 106, the information validity evaluation unit 108, and the inference means selection unit 110.

Based on the training data obtained by the training data obtainment unit 102, the inference performance evaluation unit 106 evaluates the inference performance of each of the inference means candidates created by the inference means candidate creation unit 104. The inference performance evaluation unit 106 outputs results of the evaluations to the inference means selection unit 110.

Based on the training data obtained by the training data obtainment unit 102, the information validity evaluation unit 108 evaluates the validity of information presented by the inference means candidates, for each of the inference means candidates created by the inference means candidate creation unit 104. The information validity evaluation unit 108 outputs results of the evaluations to the inference means selection unit 110.

The inference means selection unit 110 selects an inference means from the inference means candidates created by the inference means candidate creation unit 104. Specifically, the inference means selection unit 110 selects an inference means from the plurality of inference means candidates based on the inference performance evaluated by the inference performance evaluation unit 106 and the validity of the information evaluated by the information validity evaluation unit 108.

Figure 2:
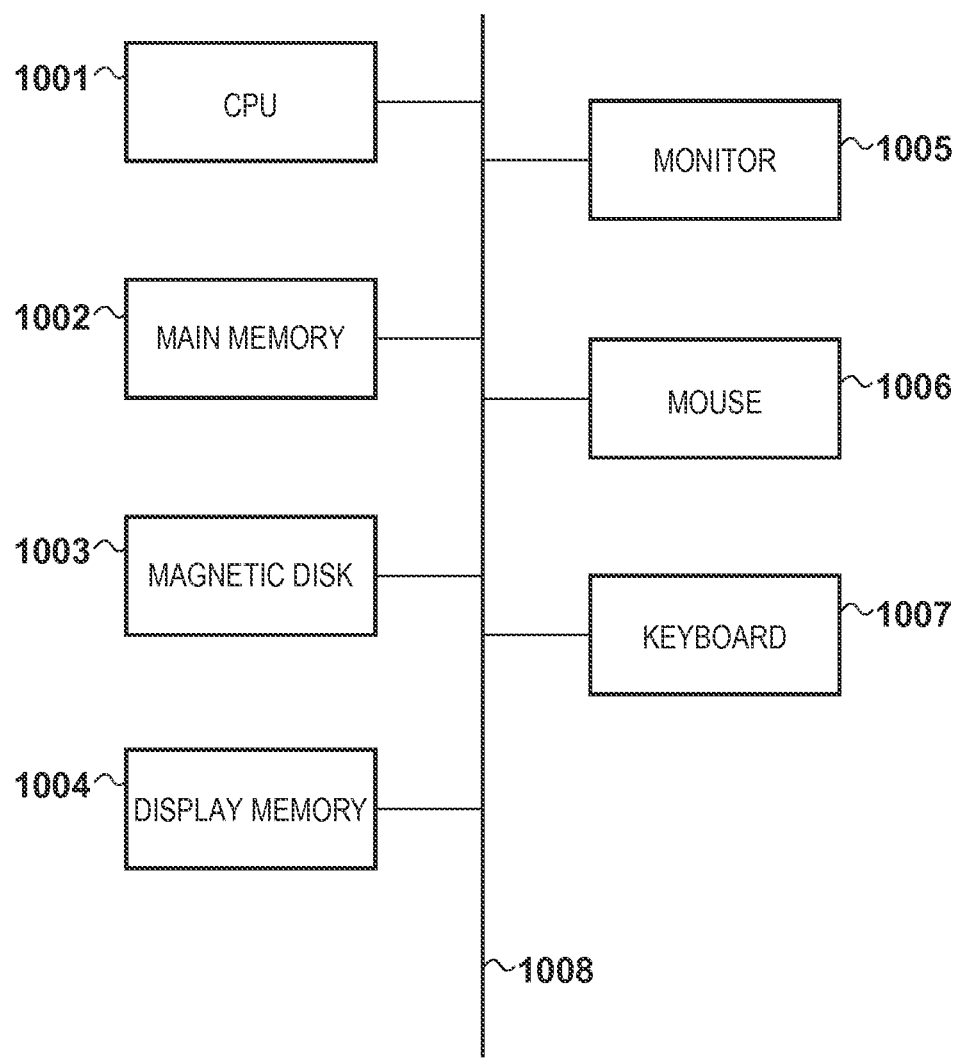
FIG. 2 is a diagram illustrating the basic configuration of a computer that realizes various processing units of the medical diagnosis support apparatus through software.

FIG. 2 is a diagram illustrating the basic configuration of a computer that implements the respective functions of the units illustrated in FIG. 1 by executing software. A CPU 1001 primarily controls operations performed by the respective constituent elements. A main memory 1002 stores control programs executed by the CPU 1001, provides a working area used when the CPU 1001 executes programs, and so on. A magnetic disk 1003 stores an operating system (OS), devices drivers for peripheral devices, various types of application software including programs for executing processes and the like (described later), and so on. A display memory 1004 temporarily stores display data. A monitor 1005 is a CRT monitor, a liquid-crystal monitor, or the like, and displays images, text, and the like based on data from the display memory 1004. A mouse 1006 and a keyboard 1007 carry out pointing inputs and character inputs from a user. The aforementioned constituent elements are communicably connected to each other over a common bus 1008.

Next, overall processing performed by the medical diagnosis support apparatus 100 will be described using the flowchart in FIG. 3. In the present embodiment, the CPU 1001 implements the functions of the various units by executing programs stored in the main memory 1002 that implement those functions. This process is generally called the Markov chain Monte Carlo method.

Note that the following descriptions assume that the image findings and clinical information names are expressed as $I_j$ (j=1 to m), and that m types of image findings and clinical information names $I_1$ to $I_m$ are handled. Furthermore, k states that can be taken on by $I_j$ are represented by $S_{jk}$. The range of k takes on various values depending on $I_j$. The present embodiment assumes as an example that the image findings and clinical information shown in FIG. 4 can be obtained. Furthermore, the present embodiment assumes that the respective image findings and clinical information can take on the states shown in FIG. 4. For example, "shape" in I1 indicates the shape of the abnormal shadow, and can take on three states, namely "round" in S11, "lobulate" in S12, and "irregular" in S13. "Lobation" in I2 expresses the degree of lobation in the abnormal shadow. "Wrap (respiratory system)" in I1 expresses whether or not there is deformation in the respiratory system in the abnormal shadow. "Past illness" in Im expresses whether or not the patient has had the illness in the past.

In the following descriptions, a set of $S_{jk}$ is indicated by E. However, it is assumed that a plurality of like elements cannot be present simultaneously in a single set E of states $S_{jk}$ for a single $I_j$. For example, in the case where I1 can be S11, S12, and S13 and I2 can be S21, S22, S23, and S24, E can be {S11, S21} but cannot be {S11, S12}. This is because a single image finding/piece of clinical information can only have a single state. Furthermore, in the following descriptions, the diagnosis is indicated using the letter D. In the present embodiment, the diagnosis can take on three values, namely "primary lung cancer", "cancer spread to lung", and "other", and these are expressed as D1, D2, and D3, respectively. An inference probability of a diagnosis Dr (r=1, 2, 3) in the case where a set E has been supplied as the input information is expressed as P(Dr|E). Likewise, a subset of E (the subset indicating information to be presented) is expressed as Ex, and an influence degree of Ex on the diagnosis Dr is expressed as I(Dr|Ex).

Meanwhile, various existing inference methods can be used for the inference means, such as a Bayesian network, a neural network, a support vector machine, or the like; in the present embodiment, a Bayesian network is used as the inference means. The Bayesian network is an inference model having a graph structure that uses conditional probabilities, through which an inference probability for each diagnosis (the probability that a given example is each diagnosis; also called a posterior probability) can be obtained when input information is input.

FIGS. 5A to 5D are diagrams illustrating an example of a Bayesian network configured from I1 to Im and D. Each variable (I1 to Im and D) is expressed as a node (a circle), and relationships between each node are expressed as arrows, called links. The node at the base of an arrow is called a parent node, whereas the node at the point of an arrow is called a child node. The relationship between a parent node and a child node expresses a conditional probability that takes the parent node as a condition. In a Bayesian network, the posterior probability of a desired variable is obtained by calculating a probability propagation using the conditional probability between variables based on inputs to the variables. When the graph structure changes, the relationships between the variables change, and the probability propagation paths change as well, resulting in different posterior probabilities being ultimately obtained. In the present embodiment, the variable to be found is assumed to be D, and thus probabilities for each diagnosis D1, D2, and D3 of the abnormal shadow, which correspond to the states of D, are obtained as inference results. A plurality of Bayesian networks having different graph structures are constructed as the inference means candidates.

Furthermore, the following descriptions assume that whether the subset Ex is negative information or positive information is determined in response to the influence degree of the subset Ex. In the present embodiment, the influence degree is calculated using a probability of each diagnosis with no input (also called a "prior probability"), an inference probability in the case where the subset Ex is input, and the number of elements in the subset Ex. For example, a influence degree I(Dr|Ex) of the subset Ex on the diagnosis Dr is calculated through the following equation. Note that P(Dr) represents the prior probability of the diagnosis Dr and C(Ex) represents the number of elements in the subset Ex.

$$I(D_r | E_x) = \frac{P(D_r | E_x) - P(D_r)}{C(E_x)} \quad (1)$$

In the case where the influence degree I(Dr|Ex) is positive, or in other words, in the case where the posterior probability when only the subset Ex is input is higher than the prior probability, the subset Ex is assumed to have a positive influence degree on the diagnosis Dr. On the other hand, in the case where the influence degree I(Dr|Ex) is negative, or in other words, in the case where the posterior probability when only the subset Ex is input is lower than the prior probability, the subset Ex is assumed to have a negative influence degree on the diagnosis Dr. Furthermore, it is assumed that the greater the absolute value of the influence degree is, the stronger the positive/negative influence will be. The present embodiment assumes that positive information is selected as the information to be presented. Note that the above methods for calculating the influence degree and selecting the information to be presented are merely examples of processing performed in the present embodiment, and the present invention is not intended to be limited thereto.

Figure 3:
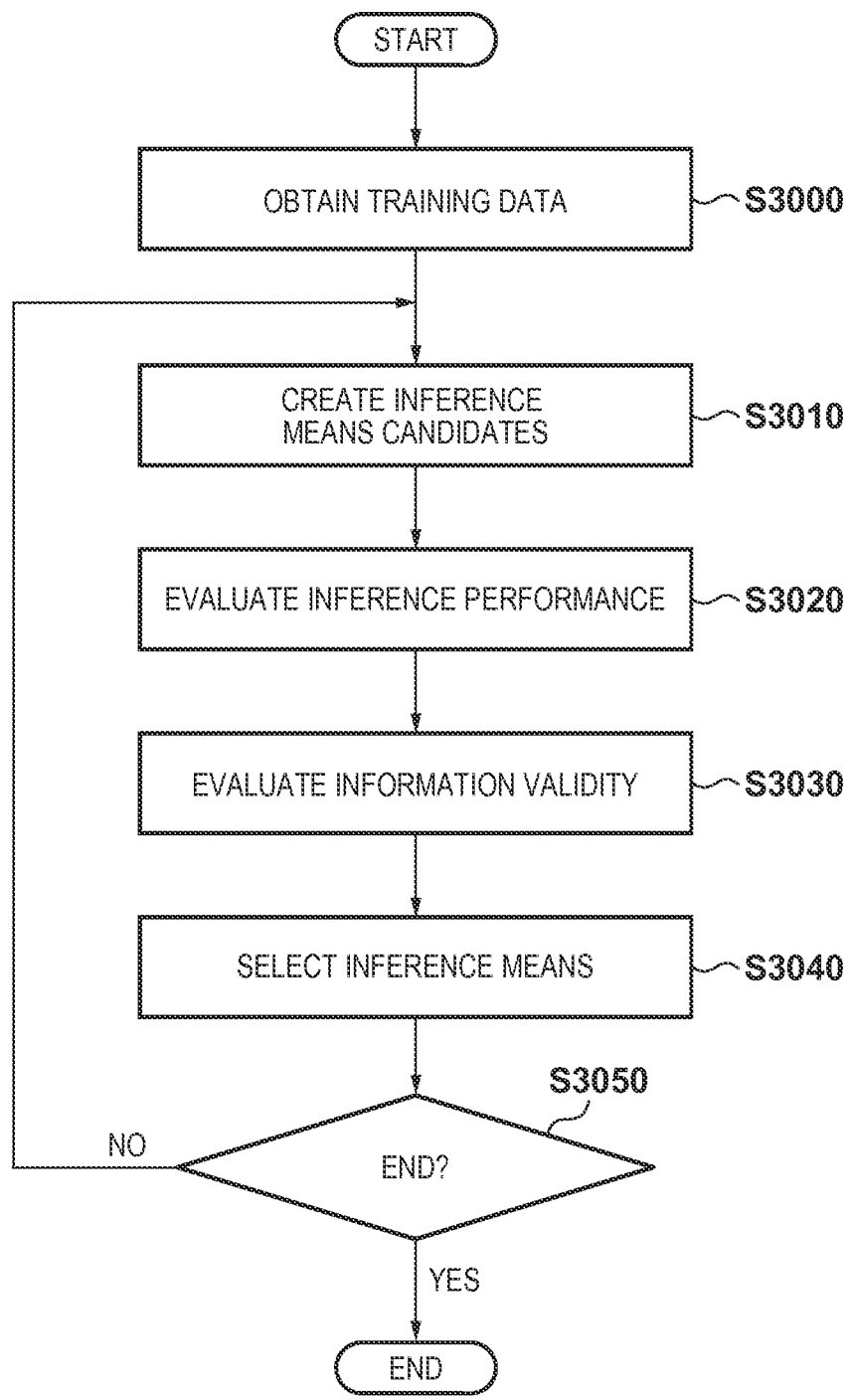
FIG. 3 is a diagram illustrating a processing sequence performed by the medical diagnosis support apparatus according to the first embodiment.

In step S3000 of FIG. 3, the training data obtainment unit 102 obtains the medical information, the finalized diagnosis, and the information of clues leading to the diagnosis for the plurality of cases regarding an abnormal shadow in a lung as the training data from the case database 200 via the LAN or the like. In the following example, it is assumed that 1,000 cases' worth of medical information, diagnosis, and information of clues leading to the diagnoses are obtained.

In step S3010, the inference means candidate creation unit 104 creates the inference means candidates based on the training data obtained in step S3000 (an inference means candidate creation step). In the present embodiment, a list of information names of the image findings and clinical information denoted in the training data (that is, Ij) is obtained, and based on that list, modifications are made to the current graph structure (indicated by "Sc" hereinafter), resulting in a provisional graph structure (indicated by "St" hereinafter). Sc and St correspond to inference means candidates. Note that in the case where the processing has advanced from step S3000 to step S3010, a graph structure such as that shown in FIG. 5A, which is configured of the information name list (I1 to Im) and D and has no links, is taken as Sc.

Figures 5A, 5B:
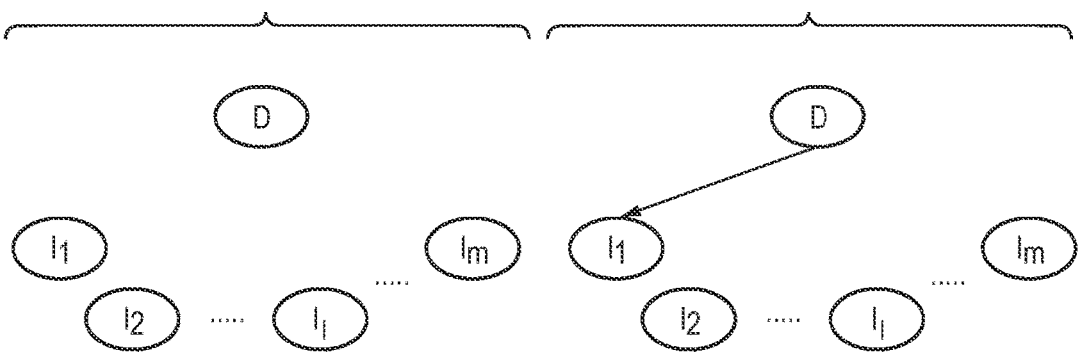
FIGS. 5A to 5D are diagrams illustrating an example of a Bayesian network.

The modification of the graph structure adds a single new link between each node (that is, I1 to Im and D), or selects a link between nodes and inverts or deletes that link. FIG. 5B shows an example in which a new link has been added from D to I1 in the graph structure shown in FIG. 5A. Of course, this modification is merely one example, and the operations are not limited thereto.

Figures 5C, 5D:
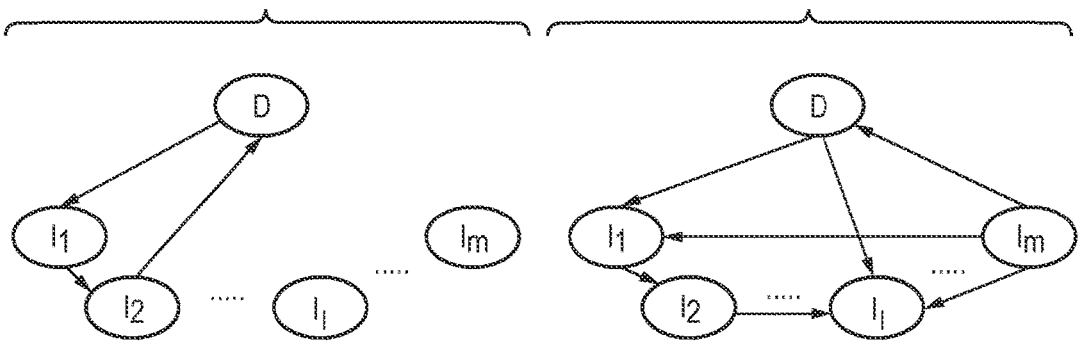

However, in the case where a Bayesian network is used, there is a problem in that the probability propagation calculation cannot be ensured if the graph structure contains a cyclic portion (as in FIG. 5C). Accordingly, it is desirable to detect cyclic portions and, in the case where a cyclic portion has been detected, discard the provisional graph structure and create a new provisional graph structure again. Such cyclic portions can be detected using an algorithm such as that proposed by Kahn.

In step S3020, the inference performance evaluation unit 106 evaluates the inference performance of the provisional graph structure St created in step S3010 based on the training data obtained in step S3000.

In the present embodiment, the inference performance is evaluated by performing five-fold cross-validation on the provisional graph structure St using the training data. The inference performance is evaluated according to an accuracy rate, by inferring the diagnosis (that is, D) using the medical information (that is, I1 to Im) and determining whether the finalized diagnosis was successfully inferred (that is, was accurate). Specifically, the diagnosis is inferred using the medical information of each case in the training data as the input information E. For example, assume that the medical information of a given case in the training data is "I1 'shape': S12 'lobulate'; I2 'lobation': S22 'strong'; . . . Il 'wrap (respiratory system)': Sl1 'yes'; . . . Im 'past illness': Sm2 'no'". In this case the input information E is E={S12, S21, . . . Sl1, . . . Sm2}. Note that the diagnosis inferred when the input information E is input is assumed to be the diagnosis among D1, D2, and D3 that has the highest posterior probability.

As a result, in the case where the diagnosis and finalized diagnosis match for 800 cases out of the 1,000, the inference performance is 0.800. Note that evaluating according to an accuracy rate is merely an example, and the inference performance may be evaluated using another method. For example a log likelihood may be calculated using the posterior probability of the finalized diagnosis, and may be used as an evaluation of the inference performance.

In step S3030, the information validity evaluation unit 108 evaluates the information validity of the provisional graph structure St created in step S3010 based on the training data obtained in step S3000.

In the present embodiment, it is assumed that different numbers of information serving as clues for the diagnosis are provided for each case (1 to 7), and the validity of the information is evaluated by performing a five-fold cross-validation on the provisional graph structure St using the training data.

Note that in the present embodiment, all subsets of sets E having 1 or 2 elements are obtained as the subsets Ex. For example, in the case of the aforementioned example, E={S12, S21, . . . Sl1, . . . Sm2}, a total of $m + {}_mC_2$ subsets Ex are obtained, such as {S12}, {S21}, {S12, S21}, {S21, Sm2}. Then, the information presented by the provisional graph structure St is taken as all of the subsets Ex whose influence degree calculated through Formula (1) is greater than or equal to 0.05.

Meanwhile, the validity of the information is assumed to be calculated as an evaluation value called an F-measure. The F-measure is a harmonic average of a precision and a recall, is an index that takes both the precision and the recall into consideration, and takes on a value of 0 to 1. The closer the F-measure is to 1, the better the performance is. The precision indicates to what degree information of clues leading to the diagnosis is present within the information presented by the provisional graph structure St. The recall evaluates how many pieces of information the provisional graph structure St was able to present for the overall information of the clues leading to the diagnosis. The F-measure is expressed through the following formula. Note that F(St) represents the F-measure of the provisional graph structure St, N(St) represents the total number of pieces of information presented by the inference model, R(St) represents the number of pieces of information presented by the inference model that match the information serving as clues leading to the diagnosis, and $C_{all}$ represents the total number of pieces of information serving as clues leading to the diagnosis.

$$F(S_t) = \frac{2 \cdot R(S_t)}{(N(S_t) + C_{all})} \quad (2)$$

For example, consider a case where the total number of pieces of information serving as clues leading to the diagnosis in 1,000 cases is 3,000, the provisional graph structure St presents a total number of 5,000 pieces of information, and 2,000 of those match the information serving as clues leading to the diagnosis. In this case, the F-measure of the provisional graph structure St is F(St)=2×2000/(5000+3000) =0.500.

In step S3040, the inference means selection unit 110 selects an inference means based on the provisional graph structure St created in step S3010 and the current graph structure Sc (an inference means selection step). Specifically, the inference means is selected by comparing the inference performance of the provisional graph structure St evaluated in step S3020 and the validity of the information in the provisional graph structure St evaluated in step S3030 with the inference performance and the information validity of the current graph structure Sc.

In the present embodiment, the current graph structure Sc and the provisional graph structure St are compared using an evaluation value obtained through the following formula. Note that V(S) represents the evaluation value of S, Vi(S) represents the inference performance of S, and Vr(S) represents the information validity of S. In this case, Vi(S) corresponds to an accuracy rate and Vr(S) corresponds to an F-measure, but the present invention is not limited to this example. Furthermore, although the following formula is a linear combination formula for Vi(S) and Vr(S), the formula may be non-linear as well, as long as two elements are used simultaneously.

$$V(S) = \alpha \cdot V_i(S) + \beta \cdot V_r(S) \quad (3)$$

In Formula (3), α and β represent weights, and whether to prioritize the inference performance or the information validity can be set by changing the values of the weights. In the present embodiment, both Vi(S) and Vr(S) can take on values of 0 to 1, and because both are to be prioritized to the same degree, α=β=0.500. For example, in the case where the accuracy rate is 0.800 and the F-measure is 0.500, the evaluation value is V=0.500×0.800+0.500×0.500 0.650. Note that in the present embodiment, an evaluation value of the current graph structure Sc is saved through the process of step S3050, which will be mentioned later. However, the evaluation value of the current graph structure Sc is assumed to be 0 in the case where the processing never traverses step S3050.

In the present embodiment, the evaluation values of the current graph structure Sc and the provisional graph structure St are compared and the graph structure with the higher evaluation value is selected as the inference means. Here, the provisional graph structure St is selected at a certain probability only in the case where the evaluation value of the provisional graph structure St does not exceed that of the current graph structure Sc. This is, of course, merely an example, and the method is not limited thereto.

A probability Pmc is calculated through the following formula, for example.

$$P_{mc} = \exp\left(-\frac{V(S_c)}{V(S_t)} \cdot \frac{1}{\gamma^{(itr+1)}}\right) \quad (4)$$

Here, γ represents a damping rate and can take on a value of 0 to 1. Meanwhile, itr represents the number of times the processing has traversed step S3050, mentioned later. Because γ is less than 1, the value within the exp parentheses approaches —∞ as itr increases, and Pmc approaches 0 as a result. In other words, a higher probability is obtained the less the processing traverses step S3050 (mentioned later), and a lower probability is obtained the more the processing traverses step S3050.

In step S3050, the medical diagnosis support apparatus 100 determines whether or not to end the construction of the inference means. In the case where it has been determined that the construction is not to end, the graph structure of the inference means selected in step S3040 is taken as the current graph structure Sc and the evaluation value is saved. In the case where it has been determined that the construction is to end, the construction of the inference means ends.

Various methods can be used for this determination; for example, the number of times the evaluation value of the current graph structure Sc has risen consecutively in the comparison performed in step S3040 (indicating a convergence) may be used, or the number of times the processing has traversed step S3050 may be used. Other methods may be used as well.

Figure 11:
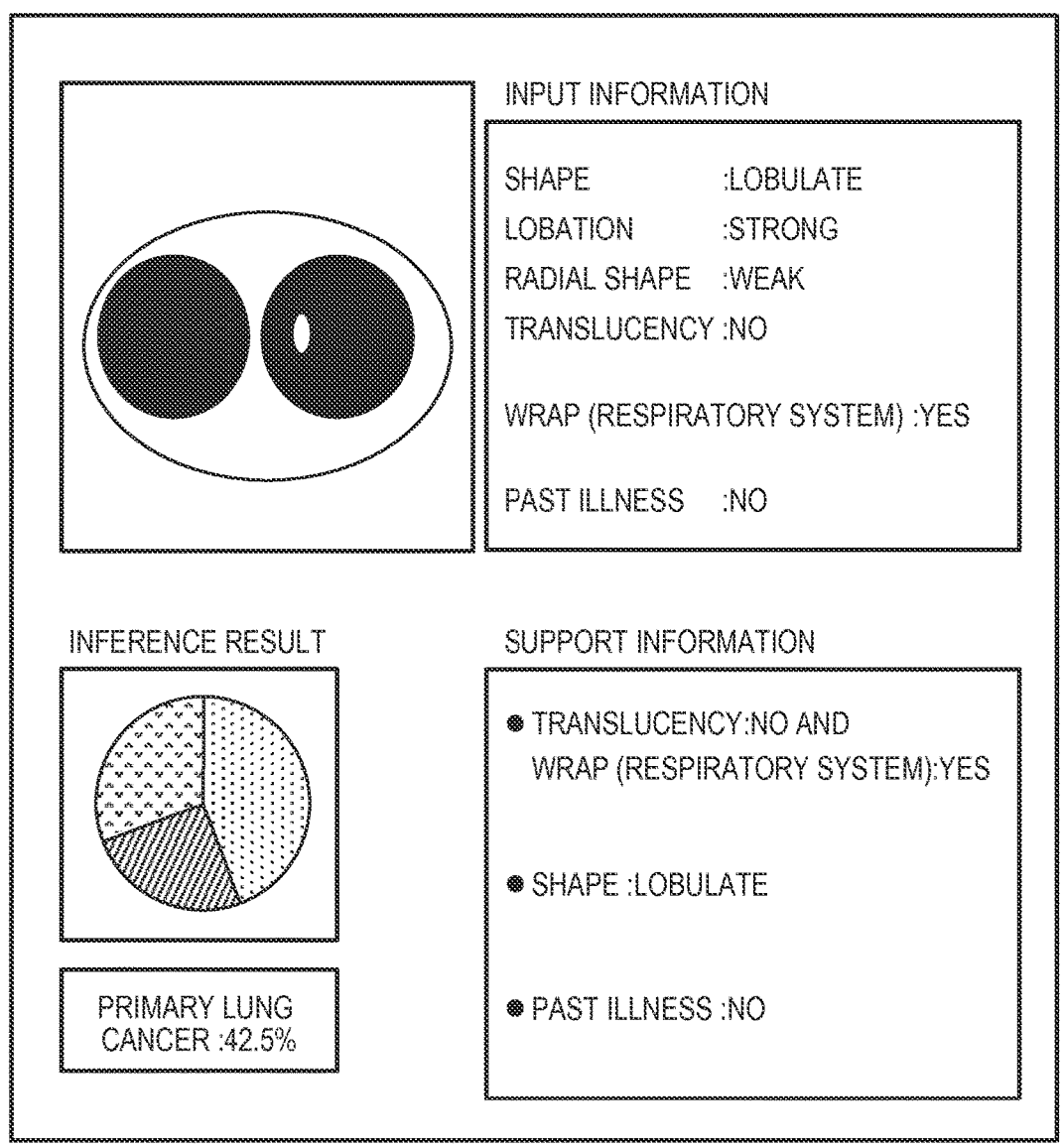
FIG. 11 is a diagram illustrating an example of the presentation of support information performed by the medical diagnosis support apparatus according to the first embodiment.

FIG. 11 illustrates an example of the presentation of support information by the medical diagnosis support apparatus using the graph structure constructed according to the procedure described in the present embodiment. According to this medical diagnosis support apparatus, the inference probability of each diagnosis is displayed as a pie chart, and positive information for the diagnosis having the highest inference probability is presented as the support information. A subjective five-level evaluation made by a doctor for this support information (5: helps with diagnosis; 3: no effect on diagnosis; 1: hinders diagnosis) indicates a more favorable result (3.9) than when using a conventional method (2.8).

According to the present embodiment, an inference means that ensures inference performance while also taking the validity of information into consideration can be constructed and selected by evaluating both the inference performance and the information validity and employing an evaluation value that meets both at the same time. Accordingly, an inference means suited to a medical diagnosis support apparatus that presents information having an effect on the inference can be constructed.

First Variation

In the present embodiment, in the case where the processing has proceeded from step S3000 to step S3010 (that is, when the processing has never traversed step S3050), a graph structure such as that shown in FIG. 5A, having no links, is taken as the initial structure Sc in step S3010. However, a graph structure created based on a doctor's knowledge or the like (as shown in FIG. 5D, for example) may be taken as the initial structure Sc.

In this case, it is desirable to calculate the evaluation value for Sc using the method indicated in step S3020, step S3030, and step S3040 prior to creating the provisional graph structure St in step S3010. It is furthermore desirable for this evaluation value to be used as the evaluation value for Sc in step S3040.

According to this method, a graph structure based on a doctor's knowledge and the like is taken as an initial value, providing an advantage of faster convergence than in the case where a graph structure having no links is used as the initial value. There is a further advantage in that a lower likelihood of excessive learning is present than in the case where a graph structure having no links is used as the initial value.

Second Variation

In the present embodiment, the provisional graph structure St is created in step S3010 by adding changes to the current graph structure Sc, and the graph structure is repeatedly selected in step S3040. In other words, the inference means is constructed using the Markov chain Monte Carlo method, as described earlier. However, the present invention is not necessarily limited to this method.

For example, the inference means may be constructed using a genetic algorithm. In this case, a plurality of genes expressing the graph structure is created in step S3010. The processing of step S3020 to step S3040 is then applied to each of the graph structures represented by the genes. Furthermore, in the case where it is determined in step S3050 not to end the construction, the processing goes through the crossover/mutation of genes in accordance with the evaluation and the selection of genes, and returns to step S3010. In the case where it has been determined to end the construction, the graph structure having genes with the highest evaluation is selected as the inference means, and the processing ends.

Alternatively, a plurality of graph structures may be created in step S3010, the respective graph structures may be evaluated through the processing of step S3020 to step S3040, and the graph structure with the highest evaluation may be selected. In this case, the processing ends without performing step S3050. Note that this may be a method in which the plurality of graph structures are created manually and selected.

Furthermore, although the present embodiment describes using a Bayesian network as the inference means and changing the graph structure to obtain the inference means candidates, another method may be employed. For example, the method may employ a variety of inference methods, such as Bayesian networks, neural networks, and decision trees, as the inference means candidates and select one of the candidates as the inference means.

Third Variation

In the present embodiment, the information validity is evaluated in step S3030 using the information serving as clues leading to the diagnosis provided for each case. However, the present invention is not necessarily limited to this method.

For example, information serving as clues leading to each diagnosis may be set in advance, and the information validity may be evaluated using a level of similarity between the information presented by the inference means and the information for the diagnoses in those cases. Alternatively, the information presented by the inference means may be evaluated subjectively, and the information validity may be evaluated based on that subjective evaluation.

Fourth Variation

In the present embodiment, when selecting the inference means in step S3040 according to the evaluation formula, the values of the weights a and p are fixed. However, the present invention is not necessarily limited to this method.

For example, the weights may be changed based on the inference performance or the evaluation value for the information validity. Specifically, when the inference performance is low, the inference performance may be prioritized by increasing $\alpha$, and when the inference performance has risen, the information validity may be prioritized by increasing $\beta$.

Alternatively, $\alpha$ and $\beta$ may be changed depending on a number of iterations (that is, the number of times the process traverses step S3010). For example, a may be increased while the number of occurrences is low, and may be reduced when the number of occurrences has become greater.

According to this method, the inference means can be selected without fixing the weights, and thus the selection of the inference means can be made more flexible.

Note that all of the variations described here can be applied to the other embodiments as well.

Second Embodiment

A medical diagnosis support apparatus according to the present embodiment updates (reconstructs) the inference means by adding data obtained during operation as additional data, in addition to the training data.

Note that the configuration of the medical diagnosis support apparatus according to the present embodiment is the same as that described in the first embodiment and illustrated in FIG. 1. Furthermore, the basic configuration of the computer that realizes the functions of the respective units in the medical diagnosis support apparatus 100 by executing software is the same as that described in the first embodiment and illustrated in FIG. 2.

Next, overall processing performed by the medical diagnosis support apparatus 100 will be described using the flowchart in FIG. 6. Note that steps in this flowchart that have the same step numbers as in the first embodiment indicate the same processes as the processes described earlier. However, part of the processing in step S3010 differs from that in the first embodiment. The following will describe only additional processes and areas that differ from those in the first embodiment.

In step S6000, the medical diagnosis support apparatus 100 constructs the inference means. This process corresponds to the processes of step S3000 to step S3050, and the details of these processes are the same as those in the first embodiment.

In step S6010, the medical diagnosis support apparatus 100 saves the additional data. Specifically, medical information is saved in a server (not shown) as an electronic health record, an interpretation report or the like while the diagnosis support apparatus is operating using the inference means created in step S6000. Periodically, pathological examination results, corresponding finalized diagnoses input by hand, and information serving as clues leading to the diagnosis are added to the saved information and saved in the case database 200.

In step S6020, the medical diagnosis support apparatus 100 performs an additional data obtainment process, and obtains, from the case database 200, cases saved in a case database after the start of operations as the additional data in addition to the training data from before the start of operations.

In step S3010, the inference means candidate creation unit 104 creates the inference means candidates based on the data obtained in step S6020. In the present embodiment, the processing is carried out using the graph structure of the inference means constructed in step S6000 as the current graph structure Sc in the case where the processing has never traversed step S3050. However, traversing step S3050 in the processing of step S6000 is ignored.

The processes of step S3020 to step S3050 are the same as the aforementioned processes, except that the evaluation is carried out using the training data as well as the additional data, rather than the training data alone. In this case, it is desirable for the weights of the evaluation formula used to select the inference means in step S3040 to be the weights used in step S6000. In the case where the weights have been made variable, the weights used when creating Sc may be saved and then used as initial values. Of course, new weights may be set, and the present invention is not limited to the examples given here.

Meanwhile, in the case where the method of the fourth embodiment (mentioned later) is applied, weights regarding the respective inference means may be saved and used as initial values.

According to the present embodiment, a more appropriate inference means can be continuously applied when divergence from the additional data has occurred by updating the inference means using data collected after the start of operations. Note that it is desirable for the processing of the present embodiment to be performed periodically at a predetermined timing. For example, performing the processing once every three months makes it possible to continuously operate an optimal medical diagnosis support apparatus.

First Variation

The present embodiment describes saving, in step S6010, the additional data used when operating the diagnosis support apparatus using the inference means constructed in step S6000. However, the data does not necessarily have to be data used during operation. For example, the data may be from another facility (database). That is, when an inference means constructed using data (a database) from a facility A is used at a facility B, the inference means may be reconstructed by adding the data (database) accumulated at the facility B as the additional data.

Second Variation

In the present embodiment, the processing in step S3010 is carried out using the graph structure of the inference means constructed in step S6000 as the current graph structure Sc in the case where the processing has never traversed step S3050. However, another method may be used as well. For example, a graph structure having no links, such as that described in the first embodiment, may be used as Sc, or another method may be employed instead.

Note that the first and second variations described here can be applied to the other embodiments as well.

Third Embodiment

A medical diagnosis support apparatus according to the present embodiment evaluates an inference means taking the structure of an inference model into consideration. Note that the configuration of the medical diagnosis support apparatus according to the present embodiment is the same as the configuration described in the first embodiment and illustrated in FIG. 1. Furthermore, the basic configuration of the computer that realizes the functions of the respective units in the medical diagnosis support apparatus 100 by executing software is the same as that described in the first embodiment and illustrated in FIG. 2.

Next, overall processing performed by the medical diagnosis support apparatus 100 will be described using the flowchart in FIG. 7. Note that steps in this flowchart that have the same step numbers as in the first embodiment indicate the same processes as the processes described earlier. However, part of the processing from step S3010 to step S3040 differs from that in the first embodiment. The following will describe only additional processes and areas that differ from those in the first embodiment.

The processes of step S3000 and step S3010 are the same as the processes described in the first embodiment.

In step S7000, the CPU 1001 of the medical diagnosis support apparatus 100 calculates distances between the respective nodes in the provisional graph structure St and saves the results of the calculations. In the present embodiment, the distance between nodes is taken as a number of links when the shortest route is taken between the nodes, assuming that the direction of the links is ignored. However, the distance is set to ∞ in the case where the route cannot be taken.

Figure 8A:
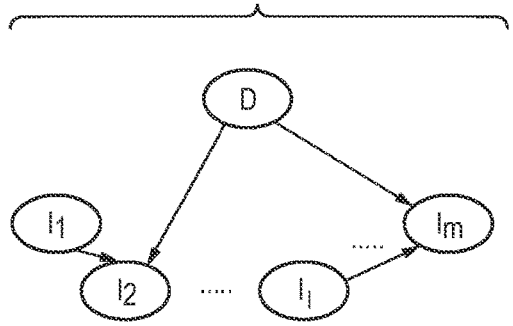
FIGS. 8A to 8D are diagrams illustrating an example of a calculation model according to the third embodiment.
Figure 8B:
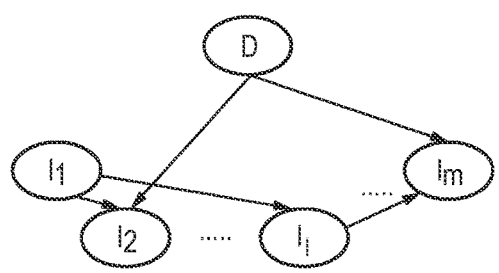
Figure 8C:
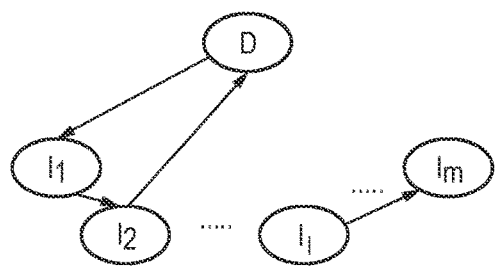

FIGS. 8A to 8D illustrate specific examples of calculating the distance from I1 to Im. In FIG. 8A, the only way to reach Im from I1 is the route I1-I2-D-Im, and thus the distance is 3. Meanwhile, in FIG. 8B, the route I1-Il-Im is available in addition to the aforementioned route, and thus taking the shortest route results in a distance of 2. In FIG. 8C, there is no route from I1 to Im, and thus the distance is ∞. This distance calculation can be carried out using the Warshall Floyd method, for example.

Figure 8D:
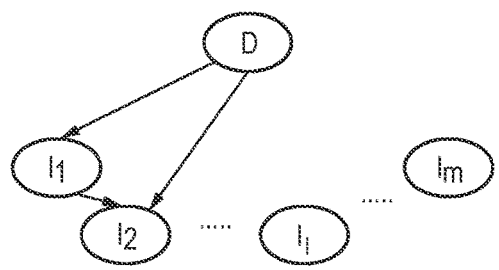

In step S7010, the inference means candidate creation unit 104 creates a calculation model St' based on the provisional graph structure St created in step S3010 and the results obtained by calculating the distances in step S7000. Specifically, from the respective nodes that indicate the information names of the image findings and the clinical information (that is, I1 to Im), nodes for which the distance from the diagnosis node D is ∞ are found based on the calculation results. In the case where there are links between the obtained nodes, those links are deleted, and the graph structure from which the links have been deleted is taken as St'. In other words, St' is created by cutting some of the links in the provisional graph structure St. For example, in FIG. 8C, Il and Im are nodes whose distance from the diagnosis node D is ∞. There is a link between Il and Im, and thus that link is deleted. A graph structure such as that illustrated in FIG. 8D is ultimately obtained.

In step S3020, the inference performance evaluation unit 106 evaluates the inference performance of the calculation model St' created in step S7010 based on the training data obtained in step S3000 and the results of the distance calculation performed in step S7000.

In the present embodiment, information E' configured of medical information corresponding to the nodes that can be reached from the diagnosis node (that is, nodes whose distances are not ∞) is created from the input information E, and the posterior probability of the diagnosis is calculated using E'. For example, in the case where E={S12, S21, . . . S11, . . . Sm2}, Il(S11) and Im(Sm2), which cannot be reached from the diagnosis node, are deleted, and thus E'={S12, S21, . . . } is created. The posterior probabilities of D1, D2, and D3 are then calculated using E'.

The inference performance is then evaluated through the same process as that in step S3020 according to the first embodiment. Note that the links between nodes that are not connected to the diagnosis node have no influence on the calculation of the probability propagation for the diagnosis. Accordingly, the inference performance of the provisional graph structure St evaluated using E, the inference performance of the provisional graph structure St evaluated using E', and the inference performance of the calculation model St' evaluated using E' are exactly the same. Because wasteful probability propagation calculation is not carried out, however, evaluating the calculation model St' using E' has the lowest calculation cost.

In step S7020, the medical diagnosis support apparatus 100 determines whether or not the inference performance obtained in step S3020 is greater than or equal to a threshold. In the case where the inference performance is greater than or equal to the threshold, the process advances to step S3030, whereas in the case where the inference performance is less than the threshold, the process advances to step S3040 without evaluating the information validity.

It is desirable for the threshold to be an evaluation of the inference performance demanded of the inference means. For example, in the case where the minimum inference performance demanded is 0.700, it is desirable for the threshold to be set to 0.700.

In step S3030, the information validity evaluation unit 108 evaluates the information validity of the calculation model St' created in step S7010 based on the training data obtained in step S3000 and the results of the distance calculation performed in step S7000.

In the present embodiment, subsets Ex having 1 to 2 elements are obtained based on the aforementioned E' and the results of the distance calculation performed in step S7000. Specifically, the subsets Ex are obtained taking into consideration the distance from the diagnosis node and, in the case where there are a plurality of elements, the distances between elements. This is based on a trend in which a shorter distance between elements has a greater influence in the probability propagation calculation using the graph structure than a longer distance between elements. In the present embodiment, subsets Ex having elements Ij whose distance from the diagnosis node is 3 or less in E' are obtained. Furthermore, in the case where there is a plurality of elements, subsets Ex that meet the aforementioned conditions and whose distance between elements is 2 or less are obtained.

Figures 9A, 9B:
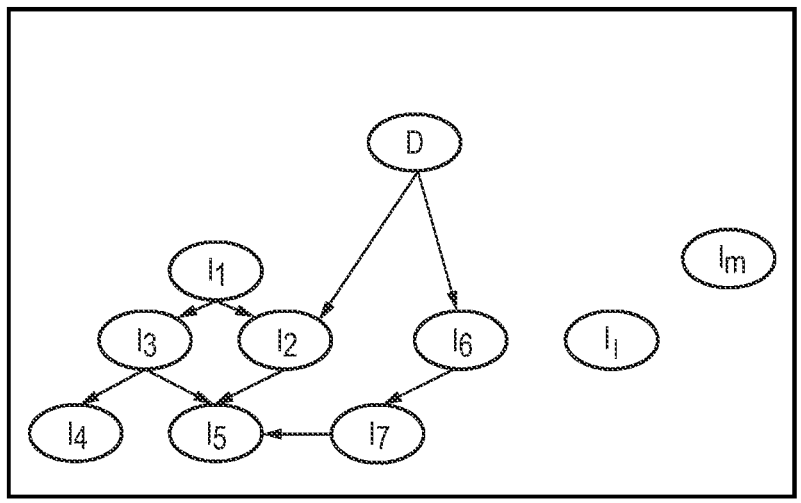
FIGS. 9A and 9B are diagrams illustrating examples of a graph structure and distance calculation according to the third embodiment.

For example, consider a case where E'={S12, S21, S33, S41, S53, S61, S72} and the calculation model St' is a graph structure such as that shown in FIG. 9A. In this case, the information whose distance from D is 3 or less are I1, I2, I3, I5, I6, I7 such as that shown in FIG. 9B, and thus {S12}, {S21}, {S33}, {S53}, {S61}, and {S72} are obtained as the subsets Ex. Meanwhile, there are 11 combinations that meet the aforementioned conditions and whose distances between nodes are 2 or less, namely (I1,I2), (I1,I3), (I1,I5), (I2,I3), (I2,I5), (I2,I6), (I3,I5), (I3, I7), (I5,I6), (I5,I7), and (I6,I7). In other words, {S12, S21}, {S12, S33}, {S12, S53}, {S21, S33}, {S21, S53}, {S21, S61}, {S33, S53}, {S33, S72}, {S53, S61}, {S53, S72}, and {S61, S72} are obtained as the subsets Ex.

The information validity is then evaluated through the same process as that in step S3030 according to the first embodiment. Through this processing, the number of subsets Ex to be considered drops and the number of probability propagation calculations drops as a result, which makes it possible to suppress the calculation costs.

In step S3040, the inference means selection unit 110 selects an inference means based on the calculation model St' created in step S3010 and the current graph structure Sc. Specifically, the inference means is selected by comparing the inference performance of St' evaluated in step S3020, the validity of the information in St' evaluated in step S3030 with the inference performance and the information validity of Sc.

The same method as that of step S3040 described in the first embodiment is used as this comparison method. However, in the case where a result of a determination performed in step S7020 has not evaluated the information validity, it is assumed that Vr(S)=0.

Meanwhile, in the present embodiment, in the case where the calculation model St' has been selected as a result of the comparison, the provisional graph structure St based on which the calculation model St' was created is selected.

The process of step S3050 is the same as the process described in the first embodiment.

According to the present embodiment, a reduction in calculation costs can be achieved while ensuring performance by reducing the number of subsets Ex used to modify the graph structure and evaluate the information validity based on reason information. Accordingly, the present embodiment is particularly useful in a situation where the model is restructured in a short period, as described in the second embodiment.

First Variation

In the third embodiment, the number of subsets Ex is suppressed in step S3030 based on the distances between the diagnosis node and each of the information nodes as well as the mutual distances between respective information nodes. However, the number may be suppressed using other methods instead.

For example, in the case where the influence is sufficiently great with partial information in which the number of elements is N, the influence will be great even if the information is not combined; accordingly, it may be determined to take that partial information alone as information influencing the derivation of the inference result, and remove that information from the candidates for element combination. Specifically, a threshold may be provided for the influence degree, and elements having an influence degree greater than or equal to the threshold may be removed from the candidates for combination. This threshold is, for example, twice the value used to determine the information presented by the provisional graph structure St. In other words, in the case where information is presented when the influence degree is greater than or equal to 0.05, the threshold is set to 0.10.

For example, consider a case in which the influence degree of {S12} is 0.12, the influence degree of {S21} is 0.04, the influence degree of {S33} is 0.02, the influence degree of {S53} is 0.11, the influence degree of {S61} is 0.21, and the influence degree of {S72} is 0.05 in the aforementioned example. In this case, {S12}, {S53}, and {S61} exceed the threshold and are thus removed from the candidates for combination. In other words, the combination is created from {S21}, {S33}, and {S72}. Considering the distances of the respective nodes, {S21, S33} and {S33, S72} are ultimately obtained as the subsets Ex with 2 elements.

Furthermore, the number of subsets Ex may be reduced using the number of nodes that are directly connected to other nodes. Specifically, nodes in a complete parent-child relationship may be removed from the candidates for combination. This will be described based on the graph structure illustrated in FIG. 10. For example, in this graph structure, if information is input in I1, the probability propagation calculation result will be the same regardless of whether information is or is not input into I2. Accordingly, in this case, it is assumed that partial information is not created by combining the respective states of I1 and I2. On the other hand, with I3, I6, and I7, I7 has probability propagation to D through I6 in a combination of I3 and I7, and thus the partial information is created based on this combination. Likewise, the partial information is created based on the combination of I6 and I7 as well. However, with the combination of I3, I6, and I7, if information is input in I3 and I6, the probability propagation calculation result will be the same regardless of whether information is or is not input into I7.

The number of subsets Ex can be further suppressed through the operations described above. Accordingly, the model can be reconstructed in a shorter time period. Note that the first variation described here can be applied to the other embodiments as well.

According to the above embodiments, an inference means that takes into consideration both the performance of the inference means and the validity of presented information can be constructed. It is furthermore possible to provide a diagnosis support technique capable of presenting appropriate information even after the start of operations by periodically updating the inference means using the additional data and taking the performance of the inference means and the validity of the presented information into consideration.

Fourth Embodiment

A medical diagnosis support apparatus according to the present embodiment constructs a final inference means by integrating a plurality of inference means created using various parameters. Note that the configuration of the medical diagnosis support apparatus according to the present embodiment is the same as the configuration described in the first embodiment and illustrated in FIG. 1. Furthermore, the basic configuration of the computer that realizes the functions of the respective units in the medical diagnosis support apparatus 100 by executing software is the same as that described in the first embodiment and illustrated in FIG. 2.

Next, overall processing performed by the medical diagnosis support apparatus 100 will be described using the flowchart in FIG. 12. Note that steps in this flowchart that have the same step numbers as in the first embodiment and the second embodiment indicate the same processes as the processes described earlier. However, part of the processing in step S6000 differs from that in the second embodiment. The following will describe only additional processes and areas that differ from those in the second embodiment.

In step S12000, the medical diagnosis support apparatus 100 sets a plurality of parameters necessary to construct the inference means in the step S6000. For example, the parameters are the values of the weights $\alpha$ and $\beta$ of the evaluation formula indicated in step S3040, the initial value of the graph structure, the method for obtaining the subsets Ex, and so on. The parameters are of course not limited to the examples given here.

In step S6000, the medical diagnosis support apparatus 100 constructs the inference means for each parameter using the plurality of parameters set in step S12000. Although the flowchart in FIG. 12 indicates the inference means being constructed in parallel, the constructions may be performed sequentially.

In step S12010, the medical diagnosis support apparatus 100 sets weights for the respective inference means constructed in step S6000. For example, the weights may be applied based on inference performance values, may be applied based on the information validity, or may be applied using another method. In the present embodiment, the same weights (that is, 1) are set for all inference means.

In step S12020, the medical diagnosis support apparatus 100 integrates the inference means based on the respective inference means constructed in step S6000 and the respective weights set in step S12010.

In the present embodiment, the integration is carried out so as to find a weighted average of the inference probability (posterior probability) and the influence degree for each inference means. Taking the posterior probability as Pu, the influence degree as Iu, and the weight as Wu for an inference means Su, a posterior probability P and an influence degree I of the integrated inference means is expressed through the following formula.

$$P = \frac{\sum (W_u \cdot P_u)}{\sum W_u}, \quad I = \frac{\sum (W_u \cdot I_u)}{\sum W_u} \quad (5)$$

For example, consider a case of three inference means and a weight of 1 for each inference means. Here, the influence degrees of the subsets Ex for the diagnosis Dr are considered, assuming that the posterior probability of the diagnosis Dr is calculated. In the case where the posterior probabilities of the respective inference means are 0.65, 0.72, and 0.69, P=(1×0.63+1×0.72+1×0.69)/(1+1+1)=0.68. Likewise, in the case where the influence degrees of Ex are 0.25, −0.13, and 0.06 respectively, I=0.06.

According to the present embodiment, a single inference means can be constructed by integrating plurality of inference means created using various parameters. Through this, a more useful inference means that offsets the advantages and disadvantages of the various parameters can be constructed.

First Variation

The present embodiment describes setting weights using the evaluation values of the inference performance and/or the validity of the inference information, or setting average weights, in step S12010. However, another method may be used as well.

For example, a doctor may make a subjective evaluation of each inference means, and the weights may be set according to that subjective evaluation. For example, a ranking may be set based on the subjective evaluation and the inverse of the ranking may be taken as the weights. That is, the weight of the inference means ranked first may be 1/1=1, the weight of the inference means ranked second may be 1/2, and so on. Alternatively, only the inference means having the highest subjective evaluation by the doctor may be employed. This corresponds to a case where the weight of the inference means having the highest subjective evaluation is 1, whereas the weights of the other inference means are 0. Meanwhile, the subjective evaluation made by the doctor may be determined through a plurality of doctors conferring, or may be determined taking in consideration of evaluations made by a plurality of doctors.

According to this method, a high weight can be set for an inference means having a high evaluation by a doctor serving as a user. Through this, an inference means that provides information more useful to the doctor can be constructed.

Second Variation

The present embodiment describes constructing a single inference means by constructing inference means in step S6000 for each of a plurality of set parameters and integrating the inference means having set weights for the respective inference means. However, another method may be used as well.

For example, a single inference means candidate may be created by creating a plurality of inference means candidates as in step S3010 described in the first embodiment and integrating the inference means candidates having set weights for the respective inference means candidates in step S3050.

Note that the first and second variations described here can be applied to the other embodiments as well.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-002094, filed Jan. 9, 2013, and Japanese Patent Application No. 2013-057306, filed Mar. 19, 2013 which are hereby incorporated by reference herein in their entirety.

What is claimed is:

1. An information processing apparatus providing an inference means for outputting a diagnosis inferred for a medical case and reason information used to infer the diagnosis, the apparatus comprising:
at least one processor; and
at least one memory, said processor and memory being operatively coupled to function as:
a first obtainment unit configured to obtain values indicating an inference accuracy or likelihood for each of a plurality of inference means based on an inference result output by each of the plural inference means and a group of first correct data including a correct diagnosis for the medical case;
a second obtainment unit configured to obtain values indicating a validity of the reason information used in the inference output by each of the plurality of inference means, based on the reason information and a group of second correct data that includes correct reason information in a case for which the correct diagnosis has been provided; and
a third obtainment unit configured to obtain at least one inference means from the plurality of inference means based on the (1) values indicating the inference accuracy or likelihood and (2) the values indicating the validity.

2. The information processing apparatus according to claim 1, wherein said processor and memory further are operatively coupled to function as a display control unit configured to display, in a display unit, the diagnosis inferred by the inference means obtained by the third obtainment unit and the reason information used to infer that diagnosis based on a plurality of pieces of identified information identified for a given case.

3. The information processing apparatus according to claim 1, wherein said processor and memory further are operatively coupled to function as a display control unit configured to display, based on a plurality of pieces of information identified for a given case, a diagnosis for the case obtained through an inference made by the inference means obtained by the third obtainment unit and the information among the plurality of pieces of identified information that has the most influence on the inference of that diagnosis, in a display unit.

4. A generating method for generating an inference means that outputs a diagnosis inferred for a medical case and reason information used to infer the diagnosis, the method comprising:
a first obtainment step of obtaining values indicating an inference accuracy or likelihood for each of a plurality of inference means based on an inference result output by each of the plural inference means and a group of first correct data including a correct diagnosis for the medical case;
a second obtainment step of obtaining values indicating a validity of the reason information used in the inference output by each of the plurality of inference means, based on the reason information and a group of second correct data that includes correct reason information in a case for which the correct diagnosis has been provided; and
a generating step of generating at least one inference means from the plurality of inference means based on (1) the values indicating the inference accuracy or likelihood performance and (2) the values indicating the validity.

5. A medical diagnosis support apparatus comprising:
at least one processor; and
at least one memory, said processor and memory being operatively coupled to function as:
a training data obtainment unit configured to obtain training data;
a candidate creating unit configured to create a plurality of inference means candidates based on the training data;
an inference performance evaluation unit configured to evaluate an accuracy or likelihood of the plurality of inference means candidates based on an inference result and correct diagnosis included in the training data;
an information validity evaluation unit configured to evaluate the validity of information presented by each of the plurality of inference means candidates based on reason information and correct reason information included in the training data; and
a selection unit configured to select an inference means from the plurality of inference means candidates based on (1) the accuracy or likelihood of the plurality of inference means candidates and (2) the validity of the information presented by each of the plurality of inference means candidates.

6. The medical diagnosis support apparatus according to claim 5, wherein the candidate creating unit is operable to create the inference means candidate as various inference methods.

7. The medical diagnosis support apparatus according to claim 5, wherein the candidate creating unit is operable to create the inference means candidates as Bayesian networks having different graph structures.

8. The medical diagnosis support apparatus according to claim 5,
wherein the candidate creating unit is operable to create the plurality of inference means candidates through processing using the Markov chain Monte Carlo method, and
the selection unit is operable to select the inference means from the plurality of inference means candidates through the processing.

9. The medical diagnosis support apparatus according to claim 5,
wherein the candidate creating unit is operable to create the plurality of inference means candidates through processing using a genetic algorithm, and
the selection unit is operable to select the inference means from the plurality of inference means candidates through the processing.

10. The medical diagnosis support apparatus according to claim 5, wherein said processor and memory further are operatively coupled to function as an additional data obtainment unit configured to obtain additional data,
wherein the inference performance evaluation unit is operable to evaluate the performance of the plurality of inference means candidates based on the training data and the additional data, and
the information validity evaluation unit is operable to evaluate the information presented by the plurality of inference means candidates based on the training data and the additional data.

11. The medical diagnosis support apparatus according to claim 10, wherein the additional data obtainment unit is operable to obtain additional data while the medical diagnosis support apparatus is operating.

12. The medical diagnosis support apparatus according to claim 10, wherein the additional data obtainment unit is operable to obtain the additional data at a predetermined timing.

13. The medical diagnosis support apparatus according to claim 10, wherein the additional data obtainment unit is operable to obtain the additional data from a database different from a database from which the training data is obtained.

14. The medical diagnosis support apparatus according to claim 5, wherein the information validity evaluation unit is operable to evaluate the validity of the information by changing processing based on the performance of the inference means candidates.

15. The medical diagnosis support apparatus according to claim 5, wherein the information validity evaluation unit is configured not to evaluate the validity of the information in the case where the performance of the inference means candidates exceeds a threshold.

16. The medical diagnosis support apparatus according to claim 7, wherein the candidate creating unit is operable to modify the graph structure based on distances from a diagnosis node in the graph structure.

17. The medical diagnosis support apparatus according to claim 7, wherein said processor and memory further are operatively coupled to function as a presenting unit configured to present information supporting a medical diagnosis based on partial information of medical information created in accordance with the graph structure.

18. The medical diagnosis support apparatus according to claim 17, wherein said processor and memory further are operatively coupled to function as a creating unit configured to create the partial information based on distances from a diagnosis node in the graph structure.

19. The medical diagnosis support apparatus according to claim 18, wherein the creating unit is operable to create the partial information based on distances between nodes in the graph structure.

20. The medical diagnosis support apparatus according to claim 5, wherein the candidate creating unit is operable to set weights for a plurality of inference means candidates created using different parameters and to construct an inference means by integrating the plurality of inference means candidates based on the weights.

21. A medical diagnosis support method for a medical diagnosis support apparatus, the method comprising:
an obtainment step of obtaining training data;
a creating step of creating a plurality of inference means candidates based on the training data;
an inference performance evaluation step of evaluating an accuracy or likelihood of the plurality of inference means candidates based on an inference result and correct diagnosis included in the training data;
an information validity evaluation step of evaluating the validity of information presented by each of the plurality of inference means candidates based on reason information and correct reason information included in the training data; and
a selection step of selecting an inference means from the plurality of inference means candidates based on (1) the accuracy or likelihood of the plurality of inference means candidates and (2) the validity of the information presented by each of the plurality of inference means candidates.

22. An information processing apparatus comprising:
at least one processor; and
at least one memory, said processor and memory being operatively coupled to function as:
a first obtainment unit configured to obtain a value indicating an inference accuracy or likelihood for an inference means based on diagnosis inferred by the inference means and a correct diagnosis;
a second obtainment unit configured to obtain a value indicating a validity of the reason information for the diagnosis inferred by the inference means, based on the reason information for the diagnosis inferred by the inference means and correct reason information; and
an evaluation unit configured to evaluate the inference means based on (1) the value indicating the inference accuracy or likelihood and (2) the value indicating the validity.

23. The medical diagnosis support apparatus according to claim 22, wherein the evaluation unit evaluates the inference means by calculating an evaluation value based on (1) the value indicating the inference accuracy or likelihood and (2) the value indicating the validity.

* * * * *